US011759649B2

(12) United States Patent
Foshee, Jr. et al.

(10) Patent No.: US 11,759,649 B2
(45) Date of Patent: Sep. 19, 2023

(54) WEARABLE CARDIOVERTER DEFIBRILLATOR HAVING ADJUSTABLE ALARM TIME

(71) Applicant: WEST AFFUM HOLDINGS DAC, Dublin (IE)

(72) Inventors: Phillip D. Foshee, Jr., Woodinville, WA (US); David P. Finch, Bothell, WA (US); Pamela Breske, Newcastle, WA (US); Laura M. Gustavson, Redmond, WA (US); Joseph L. Sullivan, Kirkland, WA (US); Jaeho Kim, Redmond, WA (US)

(73) Assignee: West Affum Holdings DAC, Dublin (IE)

(*) Notice: Subject to any disclaimer, the term of this patent is extended or adjusted under 35 U.S.C. 154(b) by 128 days.

(21) Appl. No.: 17/393,723

(22) Filed: Aug. 4, 2021

(65) Prior Publication Data
US 2021/0361961 A1 Nov. 25, 2021

Related U.S. Application Data

(62) Division of application No. 15/863,551, filed on Jan. 5, 2018, now Pat. No. 11,083,906.
(Continued)

(51) Int. Cl.
A61N 1/39 (2006.01)
A61B 5/11 (2006.01)
(Continued)

(52) U.S. Cl.
CPC ........ A61N 1/3987 (2013.01); A61B 5/02438 (2013.01); A61B 5/0816 (2013.01);
(Continued)

(58) Field of Classification Search
CPC . A61B 2562/0219; A61B 5/11; A61B 5/1123; A61B 5/282; A61B 5/361;
(Continued)

(56) References Cited

U.S. PATENT DOCUMENTS 3,724,355 A 4/1973 Busch et al.
4,583,524 A 4/1986 Hutchins
(Continued)

FOREIGN PATENT DOCUMENTS

DE 2005060985 A2 6/2007
EP 2305110 A1 4/2011
(Continued)

OTHER PUBLICATIONS

ADXL346 Data Sheet, Analog Devices, Inc., Rev. C, Nov. 2016, 41 pages.
(Continued)

Primary Examiner — Amanda K Hulbert
(74) Attorney, Agent, or Firm — Christensen O'Connor Johnson Kindness PLLC

(57) ABSTRACT

A wearable cardioverter defibrillator (WCD) having a processor configured to receive a signal indicating a position and/or movement of the ambulatory patient while the ambulatory patient is wearing the support structure receive the ECG signal, determine from an ECG signal whether a shock criterion is met, determine a confirmation time period and/or a response time period based on the position and/or movement of the ambulatory patient, determine from the ECG signal whether the shock criterion is met after the confirmation time period has elapsed, cause the user interface to generate the shock alert signal based on the shock criterion determined after the confirmation time period has elapsed, and control the discharge circuit to discharge the stored
(Continued)

electrical charge when a predetermined time period has elapsed after the shock alert signal.

11 Claims, 10 Drawing Sheets

Related U.S. Application Data

(60) Provisional application No. 62/483,617, filed on Apr. 10, 2017, provisional application No. 62/446,820, filed on Jan. 16, 2017, provisional application No. 62/442,925, filed on Jan. 5, 2017.

(51) Int. Cl.
| | |
|---|---|
| *A61B 5/08* | (2006.01) |
| *A61B 5/00* | (2006.01) |
| *A61B 5/024* | (2006.01) |
| *A61B 5/361* | (2021.01) |
| *A61B 7/00* | (2006.01) |
| *A61B 5/318* | (2021.01) |

(52) U.S. Cl.
CPC ........... *A61B 5/1116* (2013.01); *A61B 5/1117* (2013.01); *A61B 5/361* (2021.01); *A61B 5/4809* (2013.01); *A61B 5/4836* (2013.01); *A61B 5/6823* (2013.01); *A61B 5/746* (2013.01); *A61N 1/3904* (2017.08); *A61N 1/3925* (2013.01); *A61N 1/3993* (2013.01); *A61B 5/024* (2013.01); *A61B 5/318* (2021.01); *A61B 5/4812* (2013.01); *A61B 5/7203* (2013.01); *A61B 5/7275* (2013.01); *A61B 7/00* (2013.01)

(58) Field of Classification Search
CPC ..... A61B 5/363; A61B 5/6802; A61B 5/6805; A61B 5/6823; A61B 5/6831; A61B 5/7257; A61B 5/746; A61N 1/046; A61N 1/0484; A61N 1/36542; A61N 1/39046; A61N 1/3925; A61N 1/3987; A61N 1/3993
See application file for complete search history.

(56) References Cited

U.S. PATENT DOCUMENTS

| | | | |
|---|---|---|---|
| 4,619,265 A | 10/1986 | Morgan et al. |
| 4,666,432 A | 5/1987 | McNeish et al. |
| 4,698,848 A | 10/1987 | Buckley |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bornn et al. |
| 5,353,793 A | 10/1994 | Bornn |
| RE34,800 E | 11/1994 | Hutchins |
| 5,394,892 A | 3/1995 | Kenny et al. |
| 5,405,362 A | 4/1995 | Kramer et al. |
| 5,429,593 A | 7/1995 | Matory |
| 5,474,574 A | 12/1995 | Payne et al. |
| 5,618,208 A | 4/1997 | Crouse et al. |
| 5,662,690 A | 9/1997 | Cole et al. |
| 5,708,978 A | 1/1998 | Johnsrud |
| 5,741,306 A | 4/1998 | Glegyak et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,280,461 B1 | 8/2001 | Glegyak et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder et al. |
| 6,427,083 B1 | 7/2002 | Owen et al. |
| 6,437,083 B1 | 8/2002 | Brack et al. |
| 6,450,942 B1 | 9/2002 | Lapanashvili et al. |
| 6,529,875 B1 | 3/2003 | Nakajima et al. |
| 6,546,285 B1 | 4/2003 | Owen et al. |
| 6,658,292 B2 | 12/2003 | Kroll |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,559,902 B2 | 7/2009 | Ting et al. |
| 7,753,759 B2 | 7/2010 | Pintor et al. |
| 7,865,238 B2 | 1/2011 | Brink |
| 7,870,761 B2 | 1/2011 | Valentine et al. |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,527,028 B2 | 9/2013 | Kurzweil et al. |
| 8,548,557 B2 | 10/2013 | Garstka et al. |
| 8,560,044 B2 | 10/2013 | Kurzweil et al. |
| 8,615,295 B2 | 12/2013 | Savage et al. |
| 8,644,925 B2 | 2/2014 | Volpe et al. |
| 8,676,313 B2 | 3/2014 | Volpe et al. |
| 8,706,255 B2 | 4/2014 | Phillips et al. |
| 8,742,349 B2 | 6/2014 | Urbon et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,084,583 B2 | 7/2015 | Mazar et al. |
| 9,089,685 B2 | 7/2015 | Sullivan et al. |
| 9,119,547 B2 | 9/2015 | Cazares et al. |
| 9,131,901 B2 | 9/2015 | Volpe et al. |
| 9,132,267 B2 | 9/2015 | Kaib |
| 9,148,483 B1 | 9/2015 | Molettiere et al. |
| 9,265,432 B2 | 2/2016 | Warren et al. |
| 9,345,898 B2 | 5/2016 | Piha et al. |
| 9,408,548 B2 | 8/2016 | Volpe et al. |
| 9,445,719 B2 | 9/2016 | Libbus et al. |
| 9,454,219 B2 | 9/2016 | Volpe et al. |
| 9,579,020 B2 | 2/2017 | Libbus et al. |
| 9,592,403 B2 | 3/2017 | Sullivan |
| 9,598,799 B2 | 3/2017 | Shoshani et al. |
| 9,675,804 B2 | 6/2017 | Whiting et al. |
| 9,878,171 B2 | 1/2018 | Kaib |
| 9,895,105 B2 | 2/2018 | Romem |
| 9,901,741 B2 | 2/2018 | Chapman et al. |
| RE46,926 E | 7/2018 | Bly et al. |
| 10,016,613 B2 | 7/2018 | Kavounas |
| 10,076,656 B2 | 9/2018 | Dar et al. |
| 10,192,387 B2 | 1/2019 | Brinig et al. |
| 10,307,133 B2 | 6/2019 | Kaib |
| 10,463,867 B2 | 11/2019 | Kaib et al. |
| 10,589,110 B2 | 3/2020 | Oskin et al. |
| 10,599,814 B2 | 3/2020 | Landrum et al. |
| 2002/0181680 A1 | 12/2002 | Linder et al. |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2006/0173499 A1 | 8/2006 | Hampton et al. |
| 2008/0312709 A1 | 12/2008 | Vollpe et al. |
| 2009/0005827 A1 | 1/2009 | Weintraub et al. |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |

(56) References Cited

U.S. PATENT DOCUMENTS

| | | |
|---|---|---|
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0144355 A1 | 6/2013 | Macho et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0012144 A1 | 1/2014 | Crone |
| 2014/0025131 A1 | 1/2014 | Sullivan et al. |
| 2014/0046391 A1 | 2/2014 | Cowan et al. |
| 2014/0065976 A1 | 3/2014 | Jones et al. |
| 2014/0070957 A1 | 3/2014 | Longinotti-Buitoni et al. |
| 2014/0163663 A1 | 6/2014 | Poddar et al. |
| 2014/0188638 A1 | 7/2014 | Jones et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0161554 A1 | 6/2015 | Sweeney et al. |
| 2015/0297135 A1 | 10/2015 | Shoshani et al. |
| 2015/0328472 A1 | 11/2015 | Sullivan et al. |
| 2016/0004831 A1 | 1/2016 | Carlson et al. |
| 2016/0076175 A1 | 3/2016 | Rock et al. |
| 2016/0076176 A1 | 3/2016 | Rock et al. |
| 2016/0082277 A1 | 3/2016 | Foshee, Jr. et al. |
| 2016/0113581 A1 | 4/2016 | Amir et al. |
| 2016/0256104 A1 | 9/2016 | Romem et al. |
| 2016/0283900 A1 | 9/2016 | Johnson et al. |
| 2017/0014073 A1 | 1/2017 | Shoshani et al. |
| 2017/0027469 A1 | 2/2017 | Amir et al. |
| 2017/0036066 A1 | 2/2017 | Chahine |
| 2017/0040758 A1 | 2/2017 | Amir et al. |
| 2017/0162840 A1 | 6/2017 | Pendry |
| 2017/0319862 A1 | 11/2017 | Foshee, Jr. et al. |
| 2017/0367591 A1 | 12/2017 | Jorgensen |
| 2018/0116537 A1 | 5/2018 | Sullivan et al. |
| 2018/0117299 A1 | 5/2018 | Gustavson et al. |
| 2018/0184933 A1 | 7/2018 | Sullivan et al. |
| 2018/0185662 A1 | 7/2018 | Foshee, Jr. et al. |
| 2018/0243578 A1 | 8/2018 | Volosin |
| 2018/0361165 A1 | 12/2018 | Jaax et al. |
| 2019/0030352 A1 | 1/2019 | Sullivan et al. |
| 2019/0076666 A1 | 3/2019 | Medema |
| 2019/0116896 A1 | 4/2019 | Armour et al. |
| 2019/0321650 A1 | 10/2019 | Raymond et al. |

FOREIGN PATENT DOCUMENTS

| | | | |
|---|---|---|---|
| JP | 4320257 | A | 3/2005 |
| JP | 5963767 | A | 1/2014 |
| JP | 2014526282 | A | 10/2014 |
| WO | 98/39061 | A2 | 9/1998 |
| WO | 2011/146448 | A1 | 11/2011 |
| WO | 2012/064604 | A1 | 5/2012 |
| WO | 2012/151160 | A1 | 11/2012 |
| WO | 2015/056262 | A1 | 4/2015 |

OTHER PUBLICATIONS

Activity Monitoring Solution, Analog Devices, Inc., 4 pages.

Scarlett, "Enhancing the Performance of Pedometers Using a Single Accelerometer," AN-900 Application Note, Analog Devices, Inc., Rev. 0, 16 pages.

Valero et al., ADXL346 Demo—Pedometer, "Hip Pedometer Algorithm," V2.0, Jul. 8, 2011, 16 pages.

Heartstart MRx and XL AED Algorithm—Application Note, Jul. 2001, Edition 2 Philips Healthcare, USA.

Klein, H. U., Goldenberg, I., and Moss, A. J., "Risk Stratification for Implantable Cardioverter Defibrillator Therapy: The Role of the Wearable Cardioverter-Defibrillator, Clinical update," European Heart Journal, May 31, 2013, pp. 1-14, doi:10.1093/eurheartj/eht167, European Society of Cardiology.

LIFECOR LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

Zoll, LifeVest, Proven protection from Sudden Cardiac Death, issued Mar. 27, 2018, 4 pages. Pittsburgh PA, USA.

International Search Report and Written Opinion for PCT Application No. PCT/US2015/051726, dated May 20, 2016, European Patent Office, Rijswijk, 11 pages.

FIG. 2 SAMPLE COMPONENTS OF EXTERNAL DEFIBRILLATOR

WEARABLE CARDIOVERTER DEFIBRILLATOR HAVING ADJUSTABLE ALARM TIME

CROSS REFERENCE TO RELATED PATENT APPLICATIONS

This patent application is a Divisional Application of U.S. patent application Ser. No. 15/863,551, filed Jan. 5, 2018, titled WEARABLE CARDIOVERTER DEFIBRILLATOR HAVING ADJUSTABLE ALARM TIME, which claims benefit of U.S. Provisional Patent Application No. 62/483,617, filed Apr. 10, 2017, titled WCD ADJUSTING ALARM TIME & THERAPY DELIVERY PER PATIENT POSTURE CHANGES ASSOCIATED WITH RHYTHM CHANGES, U.S. Provisional Patent Application No. 62/442,925 filed Jan. 5, 2017, titled EXTENDED ALARM TIME WHILE LYING DOWN, and U.S. Provisional Patent Application No. 62/446,820, filed Jan. 16, 2017, titled DETECTING WALKING IN A WEARABLE CARDIOVERTER DEFIBRILLATOR (WCD) SYSTEM; each of which is incorporated by reference herein in its entirety.

BACKGROUND

When people suffer from some types of arrhythmias, the results may be that blood flow to various parts of the body is reduced, and some arrhythmias may even result in sudden cardiac arrest (SCA), which can lead to death very quickly unless treated immediately.

People with an increased risk of SCA often receive a implantable cardioverter defibrillator (ICD). If certain types of heart arrhythmias are detected, then the ICD delivers an electric shock through the heart. However, prior to receiving the ICD, many of these patients receive a wearable cardioverter defibrillator (WCD) system. A WCD system typically includes a harness, vest, or other garment that the patient wears, as well as electronic components, such as a defibrillator and external electrodes, coupled to the garment. When the patient wears the WCD system, the external electrodes make electrical contact with the patient's skin to help determine the patient's electrocardiogram (ECG). If a shockable heart arrhythmia is detected, the defibrillator may then deliver an appropriate shock through the patient's body.

Wearable cardioverter defibrillators (WCDs) provide a warning period prior to defibrillation therapy to allow a conscious patient to divert that therapy. WCDs commonly provide two to three rate zones for therapy treatment. For example, a lower rate zone may be provided for ventricular tachycardia (VT) and a higher rate zone for ventricular fibrillation (VF). In some WCDs, an option may be provide to monitor a zone lower than the VT zone or not to treat rhythms detected within the VT zone.

When a VF rhythm is detected, a WCD sends out a rapid alarm to warn the patient and bystanders that a shock is about to occur. If there is no response from the patient to divert the therapy, a patient is assumed to be hemodynamically unstable and unconscious and the WCD delivers a needed shock therapy. If the detected rhythm is slower and the rate falls within the VT or monitoring zone, the patient is more likely to be hemodynamically stable and thus the WCD waits a longer period of time to allow the VT to self-terminate prior to sending out patient alarms and allowing the patient to divert the therapy.

However, conventional WCD systems are unable to determine whether a patient is hemodynamically unstable and may not provide therapy to a patient that is within the VT zone but hemodynamically unstable. Conventional WCD systems do not provide an extended response time when a patient is sleeping. A sleeping patient's reaction time may be delayed to divert therapy, due to being disoriented from sleep or from dreaming.

This disclosure addresses these and other deficiencies of the prior art.

BRIEF DESCRIPTION OF THE DRAWINGS

Aspects, features and advantages of embodiments of the present disclosure will become apparent from the following description of embodiments in reference to the appended drawings in which.

DESCRIPTION

In general, embodiments of the disclosure relate to a wearable cardioverter defibrillator (WCD), comprising a support structure configured to be worn by an ambulatory patient, an energy storage module configured to store an electrical charge, a discharge circuit coupled to the energy storage module, electrodes configured to render an electrocardiogram (ECG) signal of the patient while the ambulatory patient is wearing the support structure, a user interface configured to output an alarm in response to a shock alert signal, a motion sensor configured to output a signal indicating a position and/or movement of the ambulatory patient while the ambulatory patient is wearing the support structure; and a processor. The processor may be configured to receive the signal from the motion sensor, receive the ECG signal, determine from the ECG signal whether a shock criterion is met, determine a confirmation time period based on the position and/or movement of the ambulatory patient, determine from the ECG signal whether the shock criterion is met after the confirmation time period has elapsed, cause the user interface to generate the shock alert signal based on the shock criterion determined after the confirmation time period has elapsed, and control the discharge circuit to discharge the stored electrical charge when a predetermined time period has elapsed after the shock alert signal. For example, the processor may accelerate the confirmation time if a patient fall is detected based on the motion and/or movement of the patient.

In some embodiments, the processor may be configured to determine a response time period based on the position and/or movement of the ambulatory patient, and in a first mode, control the discharge circuit to discharge the stored electrical charge after the response time period has elapsed and a user input has not been received at the user interface, and in a second mode not control the discharge circuit to discharge the stored electrical charge after the user input has been received at the user interface prior to the response time elapsing. For example, the processor may extend the response time if a sleeping state of the patient is detected based on the motion and/or movement of the patient.

A WCD system made according to embodiments disclosed herein has a number of components. These components can be provided separately as modules that can be interconnected, or can be combined with other components, etc.

Figure 1:
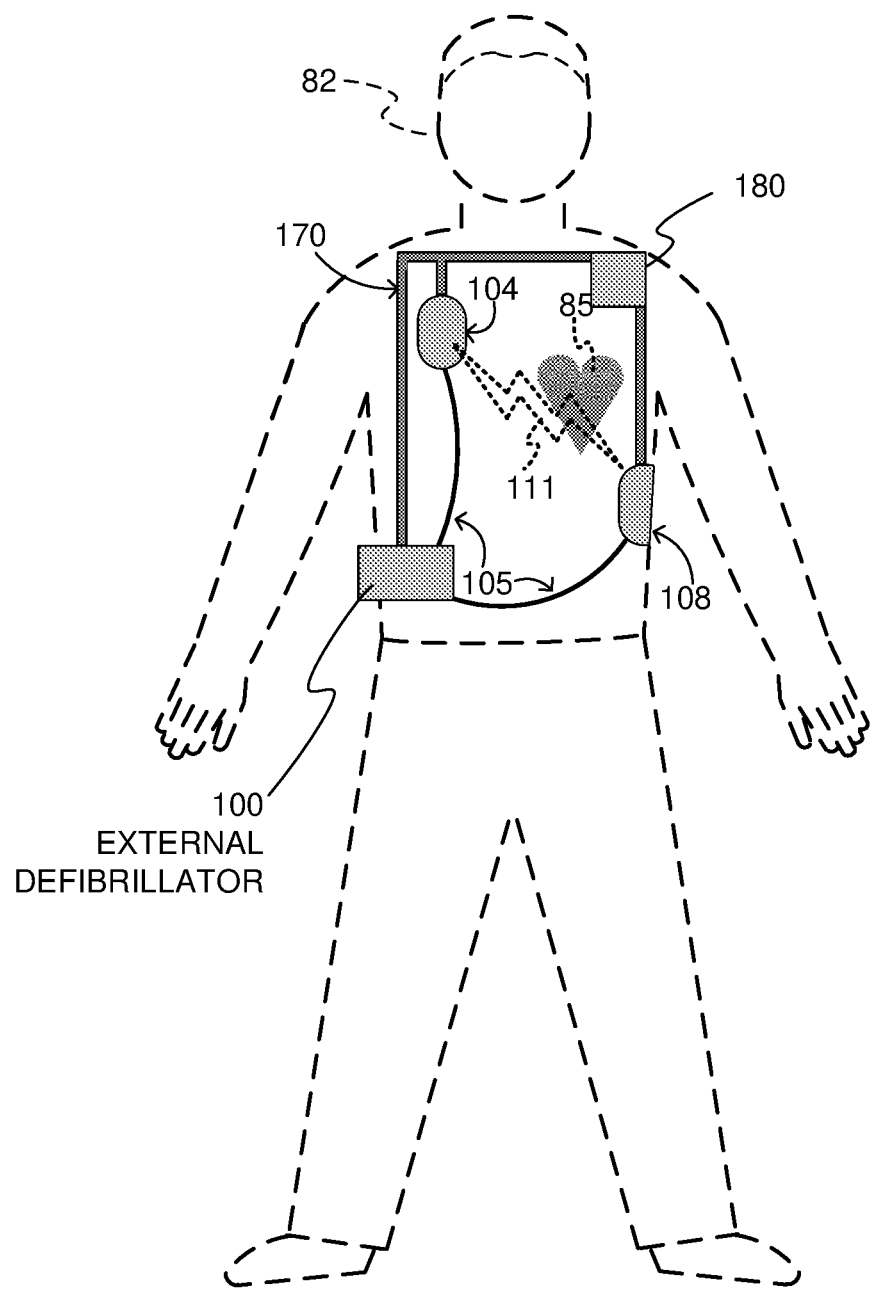
FIG. 1 is a diagram of components of a sample WCD system, according to embodiments of the disclosure.

FIG. 1 depicts a patient 82. Patient 82 may also be referred to as a person and/or wearer, since that patient wears components of the WCD system. Patient 82 is ambulatory, which means patient 82 can walk around and is not bedridden.

FIG. 1 also depicts components of a WCD system made according to embodiments disclosed herein. One such component is a support structure 170 that is wearable by patient 82. It will be understood that support structure 170 is shown only generically in FIG. 1. FIG. 1 is provided merely to illustrate concepts about support structure 170, and is not to be construed as limiting how support structure 170 is implemented or worn.

Support structure 170 can be implemented in many different ways. For example, it can be implemented in a single component or a combination of multiple components. In some embodiments, support structure 170 could include a vest, a half-vest, a garment, etc. Such items can be worn similarly to parallel articles of clothing. In some embodiments, support structure 170 could include a harness, one or more belts or straps, etc. Such items can be worn by the patient around the torso, hips, over the shoulder, etc. In embodiments, support structure 170 can include a container or housing, which can even be waterproof. In some embodiments, the support structure can be worn by being attached to the patient by adhesive material. Of course, in some embodiments, a person skilled in the art will recognize that additional components of the WCD system can be in the housing of a support structure instead of attached externally to the support structure.

A WCD system according to embodiments disclosed herein is configured to defibrillate a patient who is wearing it, by delivering an electrical charge to the patient's body in the form of an electric shock delivered in one or more pulses. FIG. 1 shows a sample external defibrillator 100, and sample defibrillation electrodes 104, 108, which are coupled to external defibrillator 100 via electrode leads 105. Defibrillator 100 and defibrillation electrodes 104, 108 can be coupled to support structure 170. As such, many of the components of defibrillator 100 could be therefore coupled to support structure 170. When defibrillation electrodes 104, 108 make good electrical contact with the body of patient 82, defibrillator 100 can administer, via electrodes 104, 108, a brief, strong electric pulse 111 through the body. Pulse 111, also known as shock, defibrillation shock, therapy or therapy shock, is intended to go through and restart heart 85, in an effort to save the life of patient 82. Pulse 111 can further include one or more pacing pulses, and so on.

A conventional defibrillator typically decides whether to defibrillate or not based on an ECG signal of the patient. However, external defibrillator 100 may initiate defibrillation (or hold-off defibrillation) based on a variety of inputs, with ECG merely being one of them.

Accordingly, it will be appreciated that signals such as physiological signals containing physiological data are obtained from patient 82. While the patient may be considered also a "user" of the WCD system, this is not a requirement. That is, for example, a user of the wearable cardioverter defibrillator (WCD) may include a clinician such as a doctor, nurse, emergency medical technician (EMT) or other similarly situated individual (or group of individuals). The particular context of these and other related terms within this description should be interpreted accordingly.

The WCD system may optionally include an outside monitoring device 180. Device 180 is called an "outside" device because it could be provided as a standalone device, for example, not within the housing of defibrillator 100. Device 180 can be configured to sense or monitor at least one local parameter. A local parameter can be a parameter of patient 82, or a parameter of the WCD system, or a parameter of the environment. Device 180 may include one or more transducers or sensors that are configured to render one or more physiological inputs from one or more patient parameters that it senses.

Optionally, device 180 is physically coupled to support structure 170. In addition, device 180 can be communicatively coupled with other components, which are coupled to support structure 170. Such communication can be implemented by a communication module, as will be deemed applicable by a person skilled in the art in view of this disclosure.

Figure 2:
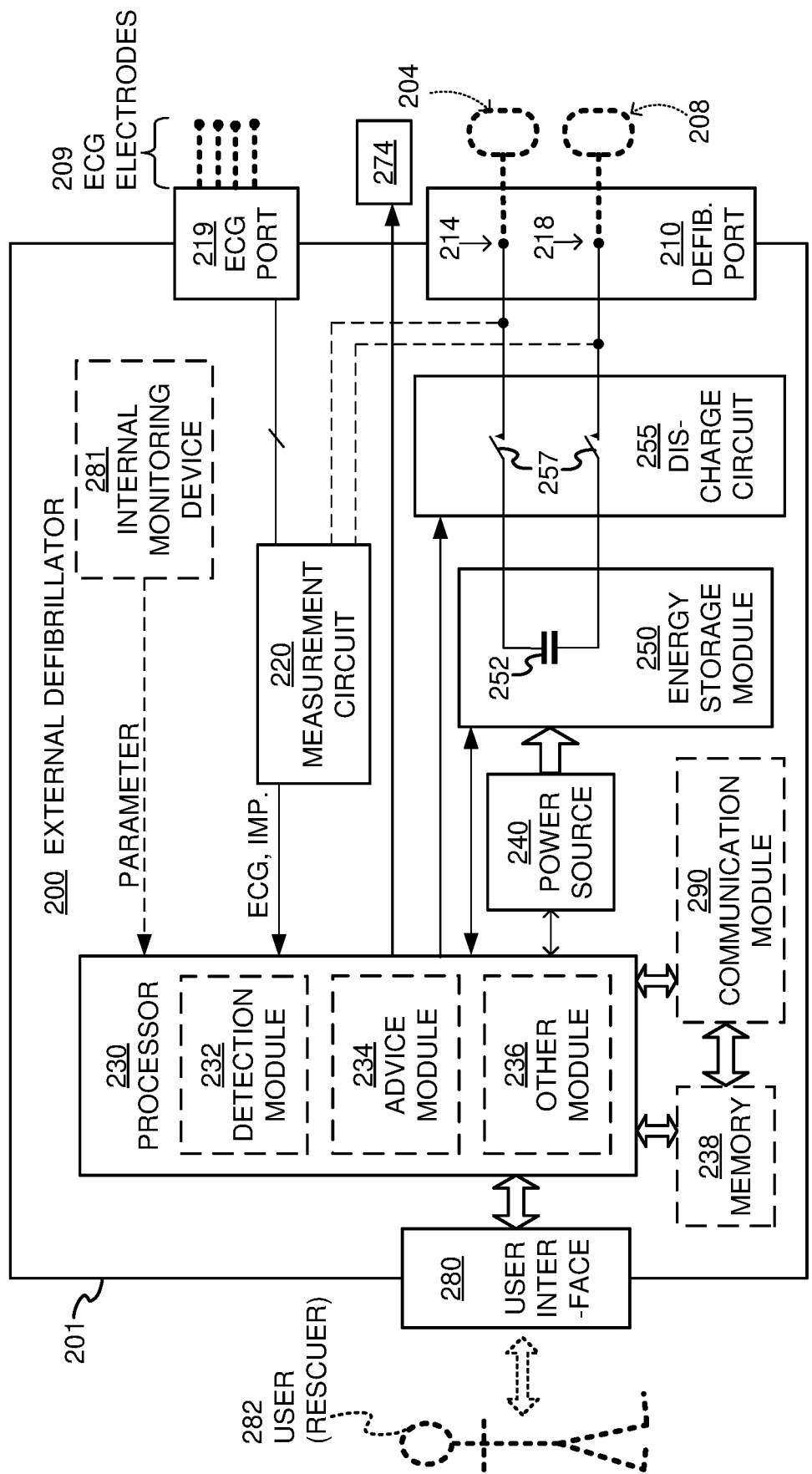
FIG. 2 is a block diagram illustrating sample components of an external defibrillator, such as the one belonging in the system of FIG. 1, according to embodiments of the disclosure.

FIG. 2 is a diagram showing components of an external defibrillator 200, made according to embodiments. These components can be, for example, included in external defibrillator 100 of FIG. 1. The components shown in FIG. 2 can be provided in a housing 201, which may also be referred to as casing 201.

External defibrillator 200 is intended for a patient who would be wearing it, such as patient 82 of FIG. 1. Defibrillator 200 may further include a user interface 280 for a user 282. User 282 can be patient 82, also known as wearer 82. Or user 282 can be a local rescuer at the scene, such as a bystander who might offer assistance, or a trained person. Or, user 282 might be a remotely located trained caregiver in communication with the WCD system.

User interface 280 can be made in a number of ways. User interface 280 may include output devices, which can be visual, audible or tactile, for communicating to a user by outputting images, sounds or vibrations. Images, sounds, vibrations, and anything that can be perceived by user 282 can also be called human perceptible indications. There are many examples of output devices. For example, an output device can be a light, or a screen to display what is sensed, detected and/or measured, and provide visual feedback to rescuer 282 for their resuscitation attempts, and so on. Another output device can be a speaker, which can be configured to issue voice prompts, beeps, loud alarm sounds to warn bystanders, etc.

User interface 280 may further include input devices for receiving inputs from users. Such input devices may additionally include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which monitoring device can be done according to design considerations. Device 281 may include one or more transducers or sensors that are configured to render one or more physiological inputs from one or more patient parameters that it senses.

Patient parameters may include patient physiological parameters. Patient physiological parameters may include, for example and without limitation, those physiological parameters that can be of any help in detecting by the wearable defibrillation system whether the patient is in need of a shock, plus optionally their medical history and/or event history. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 281 may include one or more sensors configured to acquire patient physiological signals. Examples of such sensors or transducers include electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an Sp02 sensor, and so on. In view of this disclosure, it will be appreciated that such sensors can help detect the patient's pulse, and can therefore also be called pulse detection sensors, pulse sensors, and pulse rate sensors. In addition, a person skilled in the art may implement other ways of performing pulse detection. In such cases, the transducer includes an appropriate sensor, and the physiological input is a measurement by the sensor of that patient parameter. For example, the appropriate sensor for a heart sound may include a microphone, etc.

In some embodiments, the local parameter is a trend that can be detected in a monitored physiological parameter of patient 282. A trend can be detected by comparing values of parameters at different times. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from Sp02 or CO2; f) respiratory function, respiratory rate, etc.; g) motion, level of activity; and so on. Once a trend is detected, it can be stored and/or reported via a communication link, along perhaps with a warning. From the report, a physician monitoring the progress of patient 282 will know about a condition that is either not improving or deteriorating.

Patient state parameters include recorded aspects of patient 282, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful m narrowing down the determination of whether SCA is indeed taking place.

A WCD system made according to embodiments may include a motion detector. In embodiments, a motion detector can be implemented within monitoring device 180 or monitoring device 281. Such a motion detector can be configured to detect a motion event. In response, the motion detector may render or generate from the detected motion event a motion detection input that can be received by a subsequent device or functionality. A motion event can be defined as is convenient, for example a change in motion from a baseline motion or rest, etc. Such a motion detector can be made in many ways as is known in the art, for example by using an accelerometer. In such cases, the patient parameter is a motion, one of the transducers may include a motion detector, and the physiological input is a motion measurement.

System parameters of a WCD system can include system identification, battery status, system date and time, reports of self-testing, records of data entered, records of episodes and intervention, and so on.

Environmental parameters can include ambient temperature and pressure. Moreover, a humidity sensor may provide information as to whether it is likely raining. Presumed patient location could also be considered an environmental parameter. The patient location could be presumed if monitoring device 180 or 281 includes a GPS location sensor as per the above.

Defibrillator 200 typically includes a defibrillation port 210, such as a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer the electrical charge that has been stored in an energy storage module 250 that is described more fully later in this document. The electric charge will be the shock for defibrillation, pacing, and so on.

Defibrillator 200 may optionally also have an ECG port 219 in housing 201, for plugging in sensing electrodes 209, which are also known as ECG electrodes and ECG leads. It is also possible that sensing electrodes 209 can be connected continuously to ECG port 219, instead. Sensing electrodes 209 are types of transducers that can help sense an ECG signal, e.g. a 12-lead signal, or a signal from a different number of leads, especially if they make good electrical contact with the body of the patient. Sensing electrodes 209 can be attached to the inside of support structure 170 for making good electrical contact with the patient, similarly as defibrillation electrodes 204, 208.

Optionally a WCD system according to embodiments also includes a fluid that it can deploy automatically between the electrodes and the patient's skin. The fluid can be conductive, such as by including an electrolyte, for making a better electrical contact between the electrode and the skin. Electrically speaking, when the fluid is deployed, the electrical impedance between the electrode and the skin is reduced. Mechanically speaking, the fluid may be in the form of a low-viscosity gel, so that it does not flow away, after it has been deployed. The fluid can be used for both defibrillation electrodes 204, 208, and sensing electrodes 209.

The fluid may be initially stored in a fluid reservoir, not shown in FIG. 2, which can be coupled to the support structure. In addition, a WCD system according to embodiments further includes a fluid deploying mechanism 274. Fluid deploying mechanism 274 can be configured to cause at least some of the fluid to be released from the reservoir, and be deployed near one or both of the patient locations, to which the electrodes are configured to be attached to the patient. In some embodiments, fluid deploying mechanism 274 is activated prior to the electrical discharge responsive to receiving activation signal (AS) from processor 230.

In some embodiments, defibrillator 200 also includes a measurement circuit 220, as one or more of its sensors or transducers. Measurement circuit 220 senses one or more electrical physiological signals of the patient from ECG port 219, if provided. Even if defibrillator 200 lacks ECG port 219, measurement circuit 220 can obtain physiological signals through nodes 214, 218 instead, when defibrillation electrodes 204, 208 are attached to the patient. In these cases, the physiological input reflects an ECG measurement. The parameter can be an ECG, which can be sensed as a voltage difference between electrodes 204, 208. In addition the parameter can be an impedance, which can be sensed between electrodes 204, 208 and/or the connections of ECG port 219. Sensing the impedance can be useful for detecting, among other things, whether these electrodes 204, 208 and/or sensing electrodes 209 are not making good electrical contact with the patient's body. These patient physiological signals can be sensed, when available. Measurement circuit 220 can then render or generate information about them as physiological inputs, data, other signals, etc. More strictly speaking, the information rendered by measurement circuit 220 is output from it, but this information can be called an input because it is received by a subsequent device or functionality as an input.

Defibrillator 200 also includes a processor 230. Processor 230 may be implemented in a number of ways. Such ways include, by way of example and not of limitation, digital and/or analog processors such as microprocessors and Digital Signal Processors (DSPs); controllers such as microcontrollers; software running in a machine; programmable circuits such as Field Programmable Gate Arrays (FPGAs), Field Programmable Analog Arrays (FPAAs), Programmable Logic Devices (PLDs), Application Specific Integrated Circuits (ASICs), any combination of one or more of these, and so on.

The processor 230 may include, or have access to, a non-transitory storage medium, such as memory 238 that is described more fully later in this document. Such a memory can have a non-volatile component for storage of machine-readable and machine-executable instructions. A set of such instructions can also be called a program. The instructions generally provide functionality by performing methods as may be disclosed herein or understood by one skilled in the art in view of the disclosed embodiments. In some embodiments, and as a matter of convention used herein, instances of the instructions may be referred to as a "module" and by other similar terms. Generally, a module includes a set of the instructions so as to offer or fulfill a particular functionality. Embodiments of modules and the functionality delivered are not limited by the embodiments described in this document.

Processor 230 can be considered to have a number of modules. One such module can be a detection module 232. Detection module 232 can include a Ventricular Fibrillation (VF) detector. The patient's sensed ECG from measurement circuit 220, which can be available as physiological inputs, data, or other signals, may be used by the VF detector to determine whether the patient is experiencing VF. Detecting VF is useful, because VF results in SCA. Detection module 232 can also include a Ventricular Tachycardia (VT) detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are captured according to embodiments, and determining whether a shock criterion is met. The determination can be made from a rhythm analysis of the captured ECG signal or otherwise.

In some embodiments, when the determination is to shock, an electrical charge is delivered to the patient. Delivering the electrical charge is also known as discharging. Shocking can be for defibrillation, pacing, and so on.

Processor 230 can include additional modules, such as other module 236, for other functions. In addition, if internal monitoring device 281 is indeed provided, it may be operated in part by processor 230, etc.

Defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. Executing is performed by physical manipulations of physical quantities, and may result in functions, operations, processes, actions and/or methods to be performed, and/or the processor to cause other devices or components or blocks to perform such functions, operations, processes, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200, or stored there after it is received by defibrillator 200.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy storage capacitor, and so on. In some embodiments, power source 240 is controlled by processor 230. Appropriate components may be included to provide for charging or replacing power source 240.

Defibrillator 200 may additionally include an energy storage module 250. Energy storage module 250 can be coupled to the support structure of the WCD system, for example either directly or via the electrodes and their leads. Module 250 is where some electrical energy can be stored temporarily in the form of an electrical charge, when preparing it for discharge to administer a shock. In embodiments, module 250 can be charged from power source 240 to the desired amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

Defibrillator 200 moreover includes a discharge circuit 255. When the decision is to shock, processor 230 can be configured to control discharge circuit 255 to discharge through the patient the electrical charge stored in energy storage module 250. When so controlled, circuit 255 can permit the energy stored in module 250 to be discharged to nodes 214, 218, and from there also to defibrillation electrodes 204, 208, so as to cause a shock to be delivered to the patient. Circuit 255 can include one or more switches 257. Switches 257 can be made in a number of ways, such as by an H-bridge, and so on. Circuit 255 can also be controlled via user interface 280.

Defibrillator 200 can optionally include a communication module 290, for establishing one or more wired or wireless communication links with other devices of other entities, such as a remote assistance center, Emergency Medical Services (EMS), and so on. Module 290 may also include such sub-components as may be deemed necessary by a person skilled in the art, for example an antenna, portions of a processor, supporting electronics, outlet for a telephone or a network cable, etc. This way, data, commands, etc. can be communicated. The data can include patient data, event information, therapy attempted, CPR performance, system data, environmental data, and so on.

Defibrillator 200 can optionally include other components.

Returning to FIG. 1, in embodiments, one or more of the components of the shown WCD system have been customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. Such baseline physiological parameters can be used to customize the WCD system, in order to make its diagnoses more accurate, since the patients' bodies differ from one another. Of course, such parameters can be stored in a memory of the WCD system, and so on.

A programming interface can be made according to embodiments, which receives such measured baseline physiological parameters. Such a programming interface may input automatically in the WCD system the baseline physiological parameters, along with other data.

As mentioned above, electrodes 209, or even electrodes 204 & 208 can be configured to render an electrocardiogram (ECG) signal of the patient, while the patient is wearing the support structure.

As mentioned above, WCD systems commonly provide two to three rate zones for therapy treatment, including a lower rate VT zone and a higher rate VF zone with an option to add a monitoring zone lower than the VT zone or an option not to treat rhythms that occurs within the VT zone. The VT zone is between a VT rate threshold and a VF rate threshold and the VF zone is above the VF rate threshold. For example, the WCD system may be programmed such that the VT rate threshold is 170 beats per minute (bpm) and the VF rate threshold is 200 bpm. When a rhythm greater than or equal to 200 bpm is detected, the WCD system waits a shot period to confirm the continued presence of the lethal rhythm and then sends out a shock alert alarm to warn the patient and bystanders of the impending shock. If there is no response from the patient to divert the therapy, the WCD system assumes the patient is unconscious and delivers a shock therapy to defibrillate the patient.

If the detected rhythm is instead between 170 bpm and 200 bpm, VT is detected and the WCD system waits a longer time period before generating a shock alert alarm. VT is more likely to self-terminate if given more time and patients may also remain conscious during VT and be able to divert therapy and call for help on their own, even if a shock is not delivered.

Some WCD systems also have a "monitor zone" that is programmed to record, but not treat, rhythms that are detected with rates lower than the VT zone. This zone may be used in addition to a VT zone or the WCD may be programmed to turn shocks off for all rhythms below the VF zone. For example, a monitor zone may be set to 135 bpm, which is lower than the 170 bpm and 200 bpm VT and VT zones discussed above, respectively. A WCD system will continuously monitor the heart rate (HR) and the current rhythm is evaluated for the existence of VTs. In this situation, a detected arrhythmia that occurs at 140 bpm would simply be stored in a memory for future analysis without treatment. This type of programming is indicated in patient's to prevent shocks from occurring for hemodynamically stable, slow VT and sinus tachycardias.

A patient's position or movement can affect how long a confirmation time should be between a shock advisory and a shock alert, as well as a response time from a patient after the shock alert. For example, if a patient is sleeping, the WCD may provide an extended response time for the patient to divert therapy since the patient may wake up disoriented. In another example, the confirmation time may be accelerated when a VT is detected and the patient falls or slumps over and remains motionless.

Figure 3:
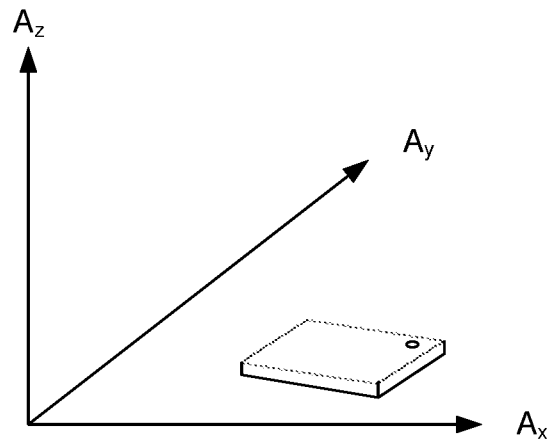
FIG. 3 is an example three-axis acceleration system for an accelerometer and the associated position of the accelerometer.

A motion sensor, such as an accelerometer, may be used to determine a patient's position and/or movement. The motion sensor may be included in one of the monitoring devices 180 and/or 281 or may be a separate component in the WCD system. FIG. 3 illustrates a three-axis acceleration measurement system for an accelerometer and the associated position of the accelerometer. As an example, the Y axis represents the up-down activity when a patient stands or sits straight up. However, as will be understood by one skilled in the art, the accelerometer may be oriented such that either one of the other axes may represent the up-down activity.

Figure 4:
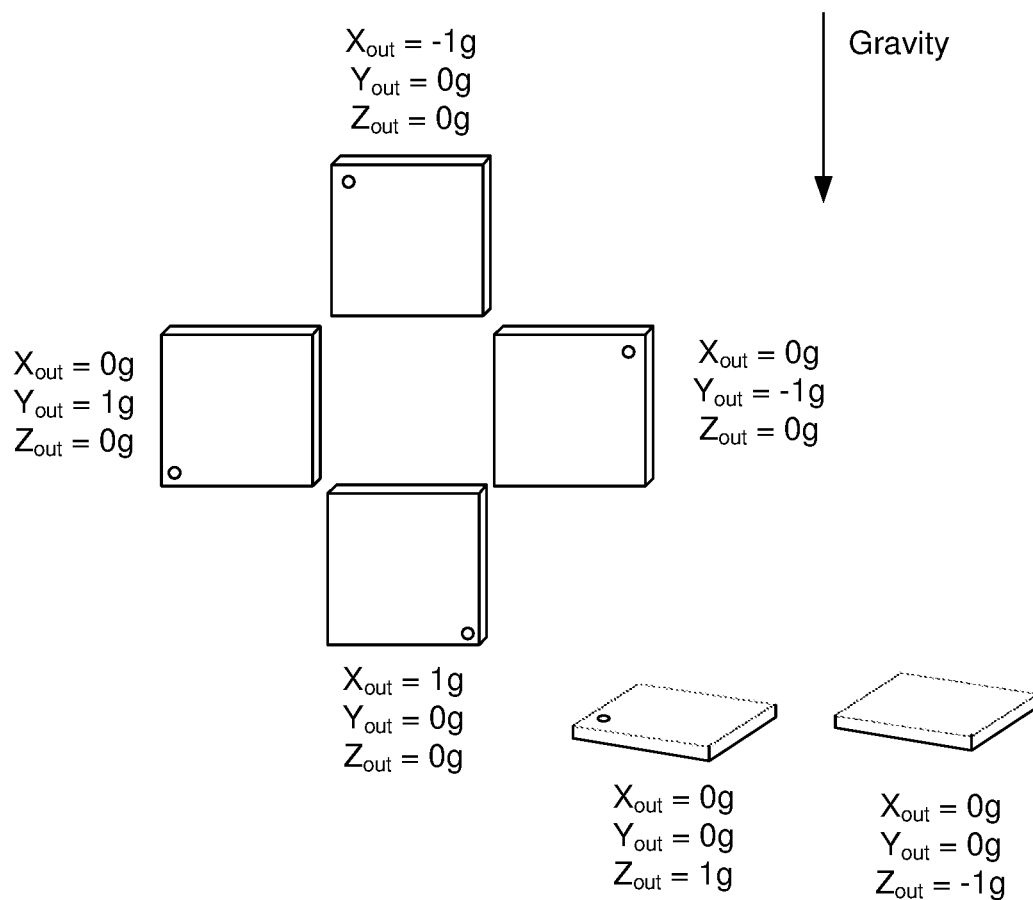
FIG. 4 is an illustration of the various orientations and outputs from the accelerometer in such orientations.

FIG. 4 illustrates the various orientation of the accelerometer and the readings provided based on the orientation shown in FIG. 3. For example, if the patient is standing or sitting upright, the $Y_{out}$ from the accelerometer will be −1 g, while $X_{out}$ and the $Z_{out}$ will be 0. When a patient is in a supine position, $Z_{out}$ is −1 g, while $X_{out}$ and $Y_{out}$ are zero. When the patient is lying on their right side, $X_{out}$ is −1 g, while $Y_{out}$ and $Z_{out}$ are zero.

A patient's actual hemodynamic status is not available to the WCD system via standard physiological measures, such as blood pressure, arterial pressure, temporal monitoring, etc. and the decision of rapid or slow therapy delivery via devices has historically been made based on the rate and/or morphology of the ECG signals. However, a surrogate for hemodynamic status may be patient posture. The WCD system disclosed herein then may shock a patient even if the heart rate is in the monitor zone or VT zone when the processor 230 detects a patient has suddenly fallen and hemodynamically instable.

Figure 5:
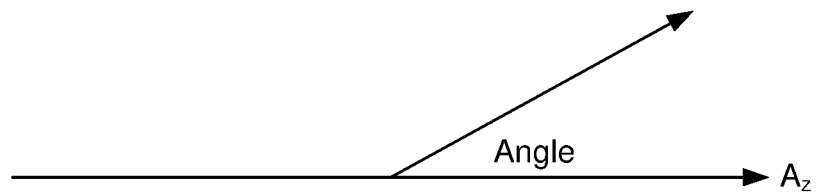
FIG. 5 is an example angle of a patient lying down from the accelerometer.
Figure 6:
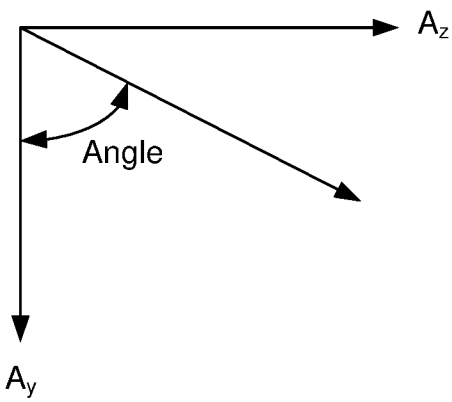
FIG. 6 is an example angle of a patient in an upright position from the accelerometer.

A patient's posture is determined to be in a lying position when an angle is thirty degrees or less from the Az axis, as shown in FIG. 5. For example, the patient is lying down when Y is between −0.5 g and 0.5 g. FIG. 6 illustrates an angle for measuring the upright position of the patient. For example, the angle would be zero when the patient is standing upright and would be ninety degrees when the patient is in the supine position. The WCD system, however, may consider any angle below thirty degrees to be an upright position in some embodiments.

Figure 7:
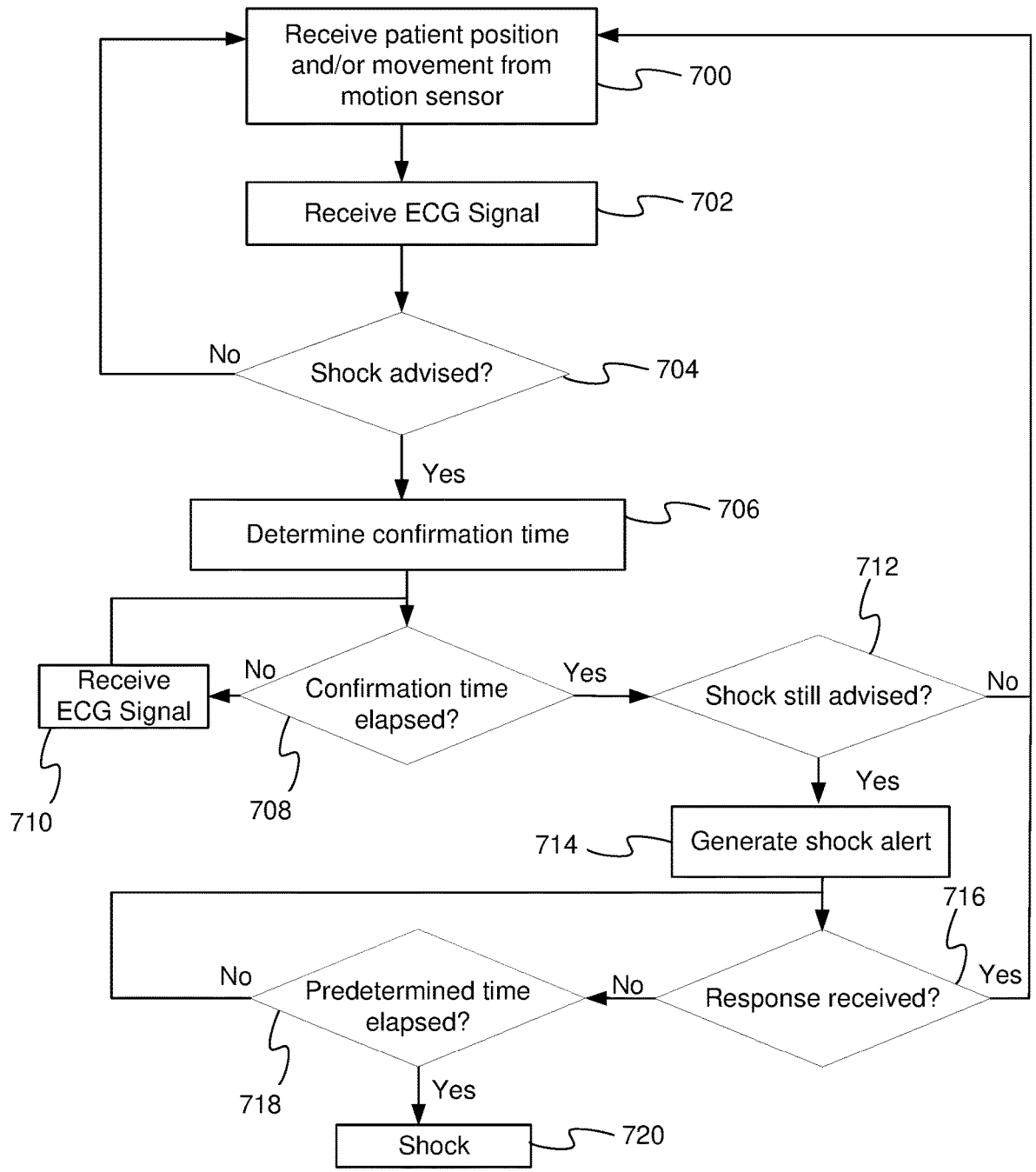
FIG. 7 is an example flow chart illustrating an example process for determining a confirmation time based on a position of a patient.

As mentioned above, the patient's posture and/or movement determined by the motion sensor may be used to detect a sudden posture change and subsequent motion, or lack thereof, after the posture change of the patient. FIG. 7 illustrates a flow chart for determining the confirmation time based on the position and/or motion.

The processor 230 receives the patient position and/or movement from the motion sensor in operation 700. The processor 230 also receives the ECG signal at operation 702. At operation 704, a rhythm analysis is performed and it is determined if a shock is advised. As shock may be advised in operation 704 if any arrhythmia is detected. In some embodiments, the shock may be advised in operation 704 if an arrhythmia is detected as well as a patient fall. In other embodiments, a shock may be advised in operation 704 if VF is detected at all, or if not VF, an arrhythmia is detected with a patient fall. That is, the shock advisory decision may be made using both the ECG signal and the position and/or movement of the patient.

Based on the posture change of the patient, as determined from the signal from the motion sensor, a confirmation time is determined to confirm the arrhythmia in operation 706. For example, in a conventional WCD system, after a VT is detected, a confirmation time may be 45 seconds to confirm VT is still present, as it may self-terminate, before generating the shock alert. If VF is detected, a confirmation time may be much shorter, such as five seconds, as VF is unlikely to self-terminate before generating the shock alert. If the motion sensor indicates that a patient has suddenly fallen, the confirmation time may be accelerated regardless of the type of arrhythmia detected.

Once the confirmation time is determined in operation 706, the processor 230 determines whether the confirmation time has elapsed in operation 708. If not, then the processor 230 continues to receive the ECG signal in operation 710. If the confirmation time has elapsed, the processor 230 determines if the shock is still advised in operation 712. This may include determining if the arrhythmia is still present and whether the signal from the motion sensor has indicated that the patient has moved after the sudden fall.

If the shock is not still advised, the processor 230 returns to operation 700. If the shock is still advised, then the processor will instruct the user interface 280 to generate a shock alert in operation 714 to warn the patient and bystanders of the impending shock. In operation 716, the processor 230 check to see if a response has been received from a user to divert therapy. If yes, then the processor 230 returns to operation 700. If not, then the processor 230 determines if a predetermined time, or response time, has elapsed in operation 718. If not, then the processor continues to check to see if a response has been received from the user to divert therapy in operation 716. If the response time has elapsed, then the processor 230 controls the discharge circuit to shock the patient in operation 720. In some embodiments, in addition to, or instead of, shocking the patient, the processor 230 may initiate a communication with a remote center, such as a hospital, 911, or any other remote center, to get necessary help. This may be especially beneficial if the detected heart rate is in the monitor zone or the VT zone.

In some embodiments, the predetermined time, or response time, may be determined based on patient movement after the detected fall. After the patient fall has been detected by the processor 230, as discussed in more detail below, the signal from the motion sensor may also be used to determine the movement of the patient after the detected fall. If the patient is not moving, then the response time may also be accelerated and the shock given more quickly after the warning. If the patient is moving, the response time may be longer and give the patient more time to divert the therapy.

A patient posture change may be detected and characterized as a patient fall by the processor 230 when the motion sensor detects that the patient was upright and then in a sitting or supine position, and a positional change threshold has been violated. The positional change threshold, for example, may be time, a force, or any combination thereof. For example, if the processor 230 determines, based on the signal from the motion sensor, that a patient was in an upright position and within five seconds or less in a sitting or supine position, this is detected as a patient fall. In some embodiments, the processor 230 may determine the fall if the patient was in an upright position and within one second or less is in a sitting or supine position. In other embodiments, the processor 230 may determine a patient fall when the signal from the motion senor indicates that the change from upright to a sitting or supine position happened greater than a threshold force. That is, the impact of the fall will show on the signal from the motion sensor. In some embodiments of the disclosure, both time and force may be used by the processor 230 to detect a patient fall.

In some embodiments, processor 230 may determine patient has fallen when in a sitting position and then in a supine or a semi-supine position without any further movement. For example, if the patient suddenly, in less time period than a positional change threshold, falls into supine or semi-supine position from a sitting position, this will be detected as patient fall and the confirmation time may be accelerated if an arrhythmia is also detected at this time.

However, a slow, normal posture change, such as getting into bed or lying down, will not be detected as a patient fall. The processor 230 would detect this as a normal change by determining the posture change did not violate the positional change threshold, for example, by not being above a certain force and taking a longer time than 5 seconds. For example, if a change over 5 seconds is greater than a threshold on the accelerometer, such as 0.5 g, then a posture change is detected, but is not characterized as a patient fall and the confirmation time is set accordingly based on any detected arrhythmia. That is, the confirmation time would be 15 seconds for VF and 45 second for detected VT.

Figure 8:
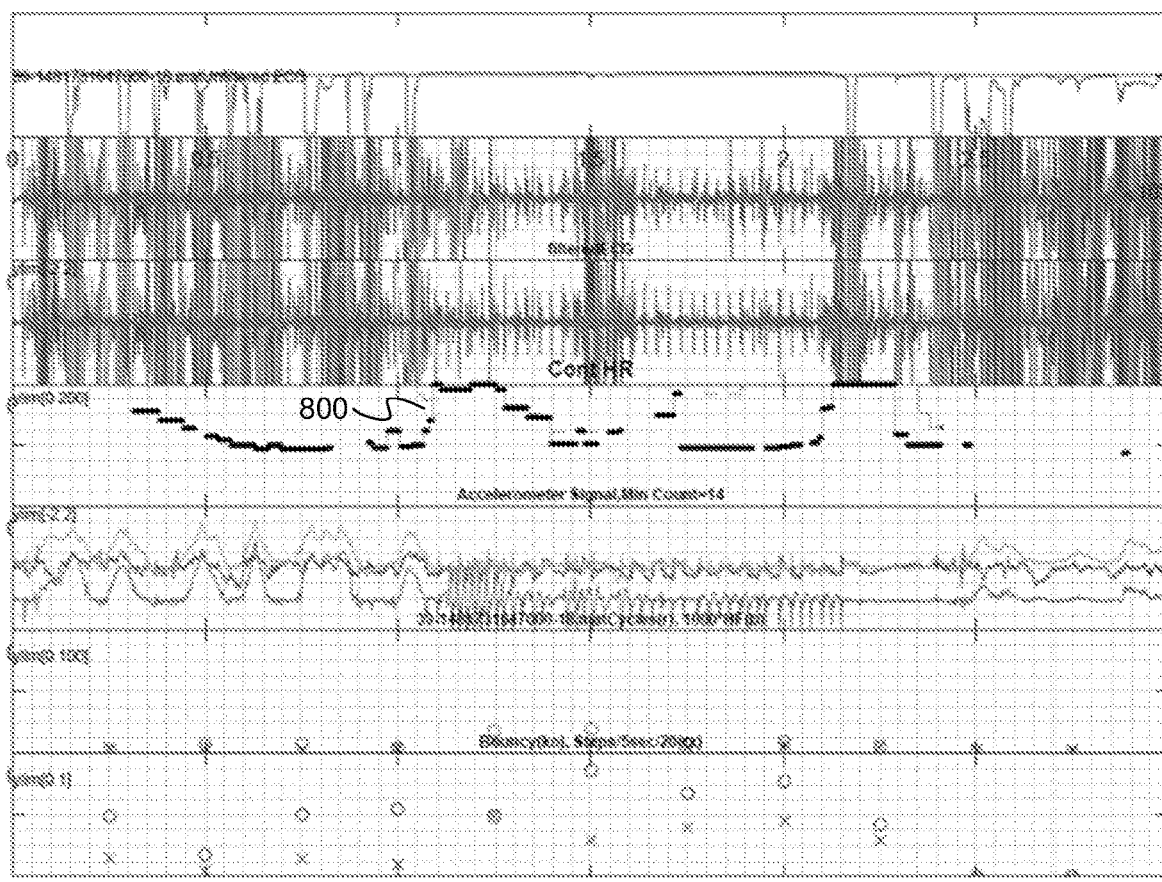
FIG. 8 is an example of measured outputs of a patient performing a slow posture change.

FIG. 8 illustrates an accelerometer showing the beginning of a posture change at 800. At the same time, significant noise is detected on the ECG signals with an elevated heart rate measured. However, since a slow posture change is detected, this is characterized as a normal posture change and the confirmation time would not be accelerated.

In some embodiments, noise may also be detected on the ECG signal, as discussed above with respect to FIG. 8. Because WCD systems use dry electrodes, the noise artifact created when a patient is moving can easily corrupt the ECG signal and the heart rate can be falsely elevated. When this is detected by the processor 230 by using noise detection, the confirmation time and response time may be longer because a patient that is making continuous postural changes is likely not in need of therapy.

Further, a patient who has fallen is unable to get up with cardiac arrhythmias with heart rates below the lowest zone and stay conscious. If this event occurs, the processor 230 evaluates the current rhythm and alerts the patient to check to see if the patient is conscious. If the patient does not respond via the user interface 280, a shock can be delivered or the processor 230 can initiate a call to a remote center to get help.

As mentioned above, the position or movement of the patient may also be used to determine a response time for a patient to divert therapy. If the processor 230 determines that a patient is sleeping based on the position and/or motion of the patient, the response time may be longer to allow the patient additional time to react to the shock alert noise and divert therapy, if desired, since the patient may be disoriented from sleeping.

Figure 9:
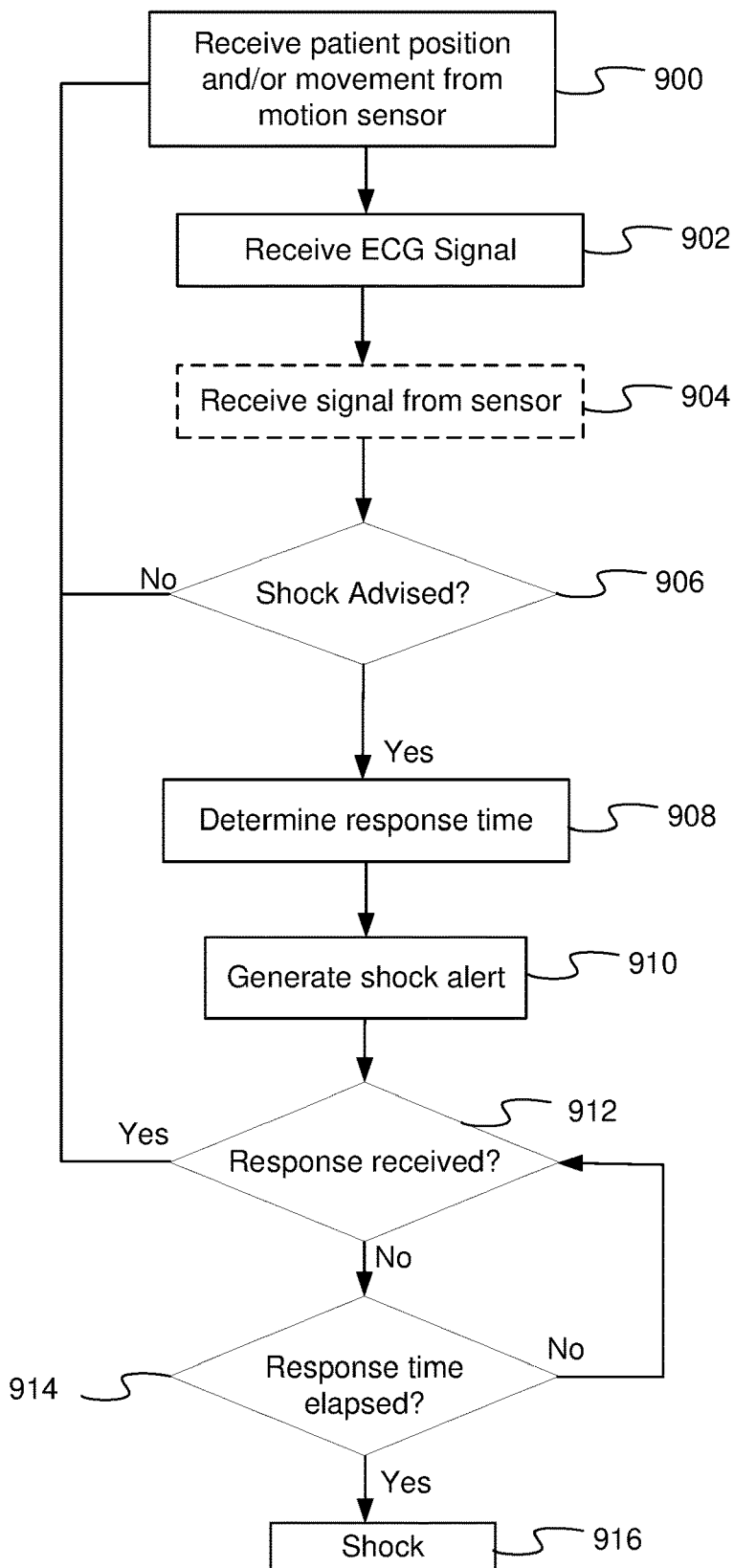
FIG. 9 is an example flow chart illustrating an example process for determining a response time based on a position of a patient.

FIG. 9 illustrates a flow chart for determining a response time based on the motion sensor signal. The processor 230 receives the patient position and/or motion from the motion sensor in operation 900. In operation 902, the processor 230 receives the ECG signal. In some embodiments, the processor 230 may also receive a signal from a physical sensor in operation 904, which will be discussed in more detail below. Based on the ECG signal, the processor 230 determines in operation 906 whether a shock is advised. While not shown in FIG. 9, this may also include confirming the shock advisory during a confirmation time that is set based on the type of arrhythmia detected, as would be understood by one skilled in the art and as discussed above with respect to FIG. 8. In operation 908, the processor 230 determines the response time based on the detected position, the ECG signal, and/or the signal from the physical sensor.

In operation 910, the processor 230 causes the user interface 280 to generate the shock alert to warn the patient and bystanders of the impending shock. In operation 910, the processor 230 checks to see if a response has been received from a user through the user interface, and if yes, the processor returns to operation 900.

If a response has not been received, in operation 914, the processor 230 determines if the response time has elapsed. If not, the processor 230 returns to operation 912 and if yes, then a shock is given to the patient in operation 916.

In some embodiments, the patient may be determined to be sleeping and an extended response time may be used when the patient has been lying in a supine position, including on the patient's side, for a greater than a minimum time duration, such as 30 minutes, for example. The minimum time duration is used because otherwise a patient may just be lying down and not asleep, or not in a deep sleep, and does not need an extended response time to respond to the shock alert.

Figure 10:
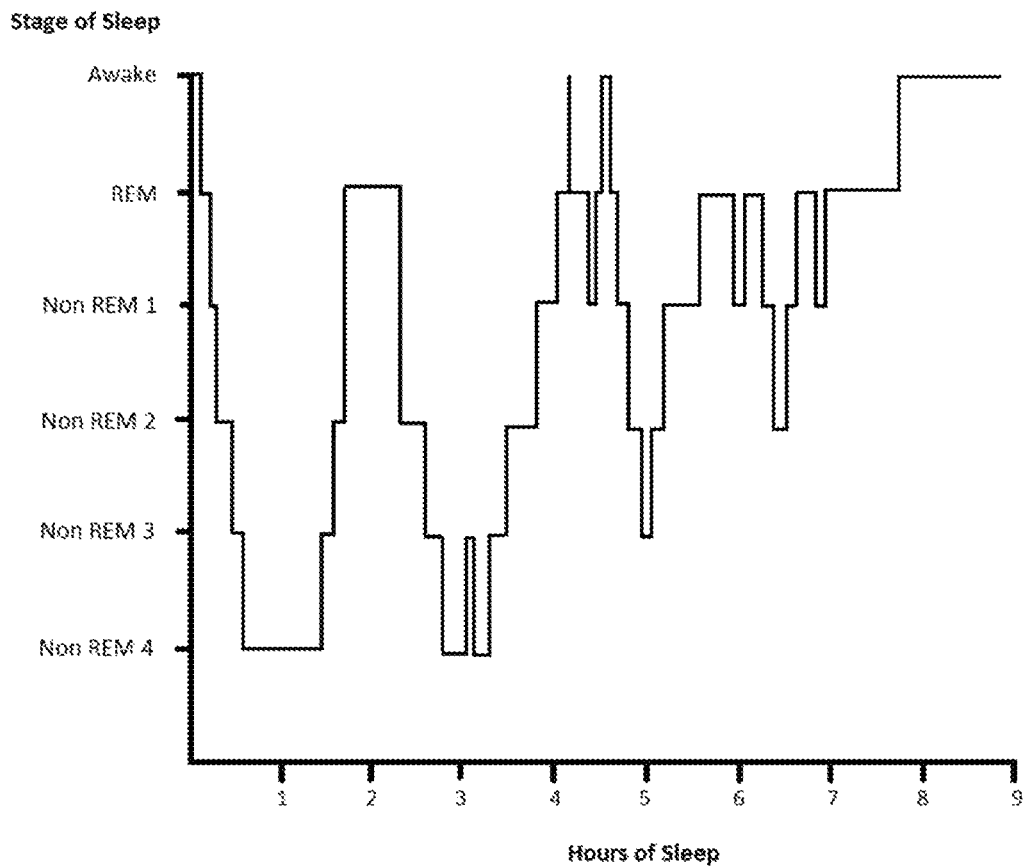
FIG. 10 illustrates a graph depicting the various stages of a sleeping patient.

FIG. 10 illustrates the various stages of sleeping, for example. It takes about 30 minutes for the patient to enter a deep sleep, which may then be used as the minimum time duration. As can be seen in FIG. 10, there is more REM sleep prior to waking. However, as would be understood by one skilled in the art, other minimum time durations may be used based on a patient's sleeping pattern.

In some embodiments, the processor 230 may also use the amount of motion of the patient based on a signal from the motion sensor to determine the patient is asleep. Motion may be determined as the sum of the absolute values of the three axes after being band pass filtered to remove any direct current (DC) values. The band pass filter may be, for example, a 1 Hz high pass filter plus a 6 Hz low pass filter. Using this band pass filter as an example then, if the activity is calculated to be less than 0.05, then it is considered as a lack of motion.

In some embodiments, heart rate may also be used as another factor by the processor 230 in determining whether a patient is asleep. Heart rate slows down when a patient sleeps, so a lower heart rate compared to when the patient entered the lying position may be used to confirm that the patient is in a deep sleep state in addition to or instead of the minimum time threshold. Further, in some embodiments, a long term trend of heart rate may be available to the processor 230 through a memory, and may be used to more accurately confirm the sleeping state of the patient.

Figure 11:
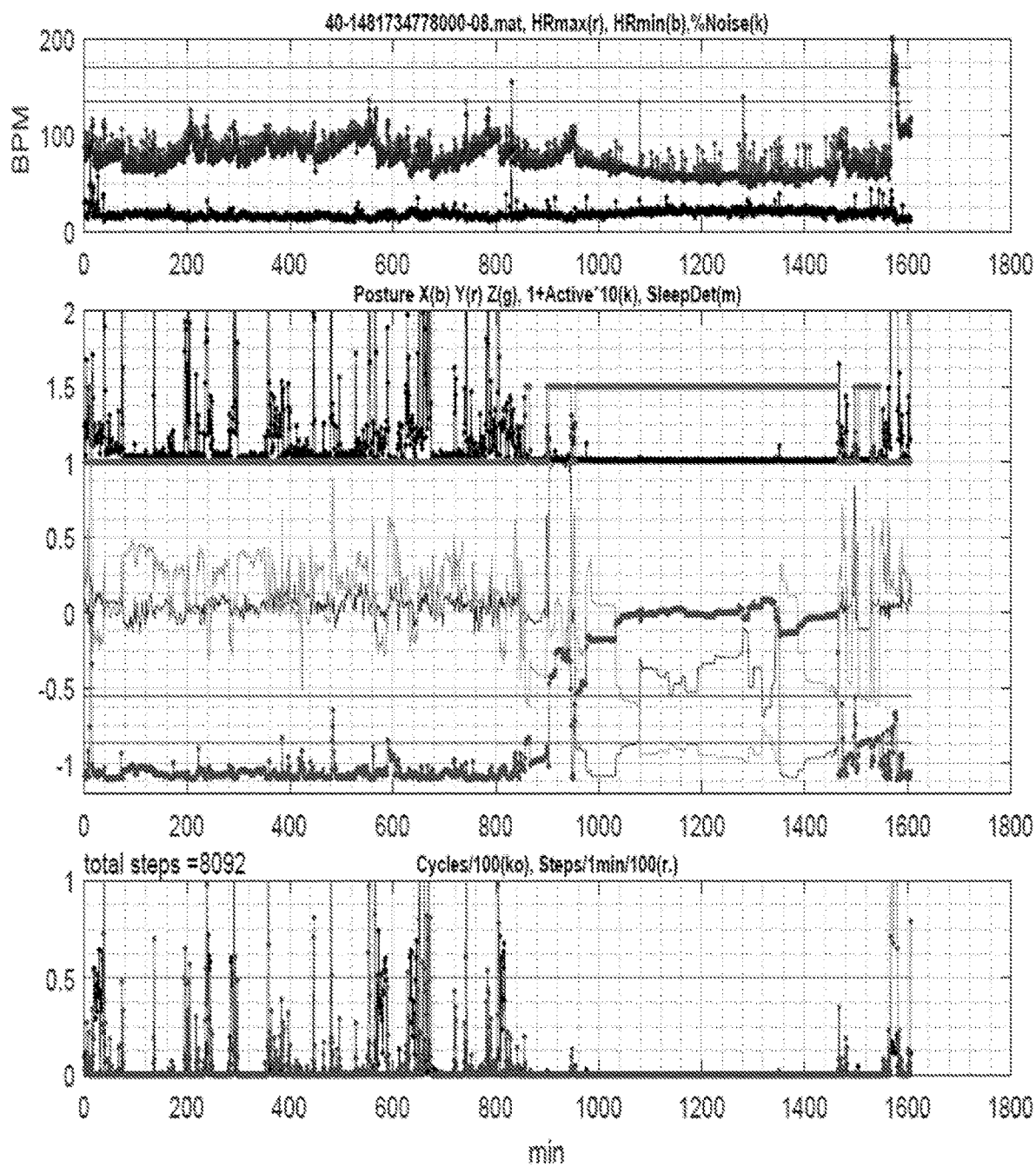
FIG. 11 illustrates an example of measured outputs of a patient to determine the patient is in a sleeping state.

FIG. 11 illustrates a sleep detection example. The top chart shows a slowing heart rate after 950 minutes. However, as seen in the second chart, the patient began lying down around 800 minutes, but the heart rate had not slowed down. This information may be used by the processor 230 to indicate that the patient is asleep at 950 minutes but not asleep at 800 minutes. That is, this examples uses both time and heart rate to determine when the patient enters the sleeping state.

Some cardiac patients may sleep in a raised position, such as in a raised bed or in a recliner. If a patient sleeps in a raised position, the angle in FIG. 6 will likely be lower than sixty degrees and higher than thirty degrees. If the angle is lower than thirty degrees, the processor 230 determines the patient is standing. If the patient is in the raised position, with a lack of motion, for example, with activity calculated, as discussed above using a high pass band filter, to be below 0.025, then the processor 230 determines the patient is asleep. That is, in a raised position, a lower activity level threshold is used to confirm the patient is asleep.

Figure 12:
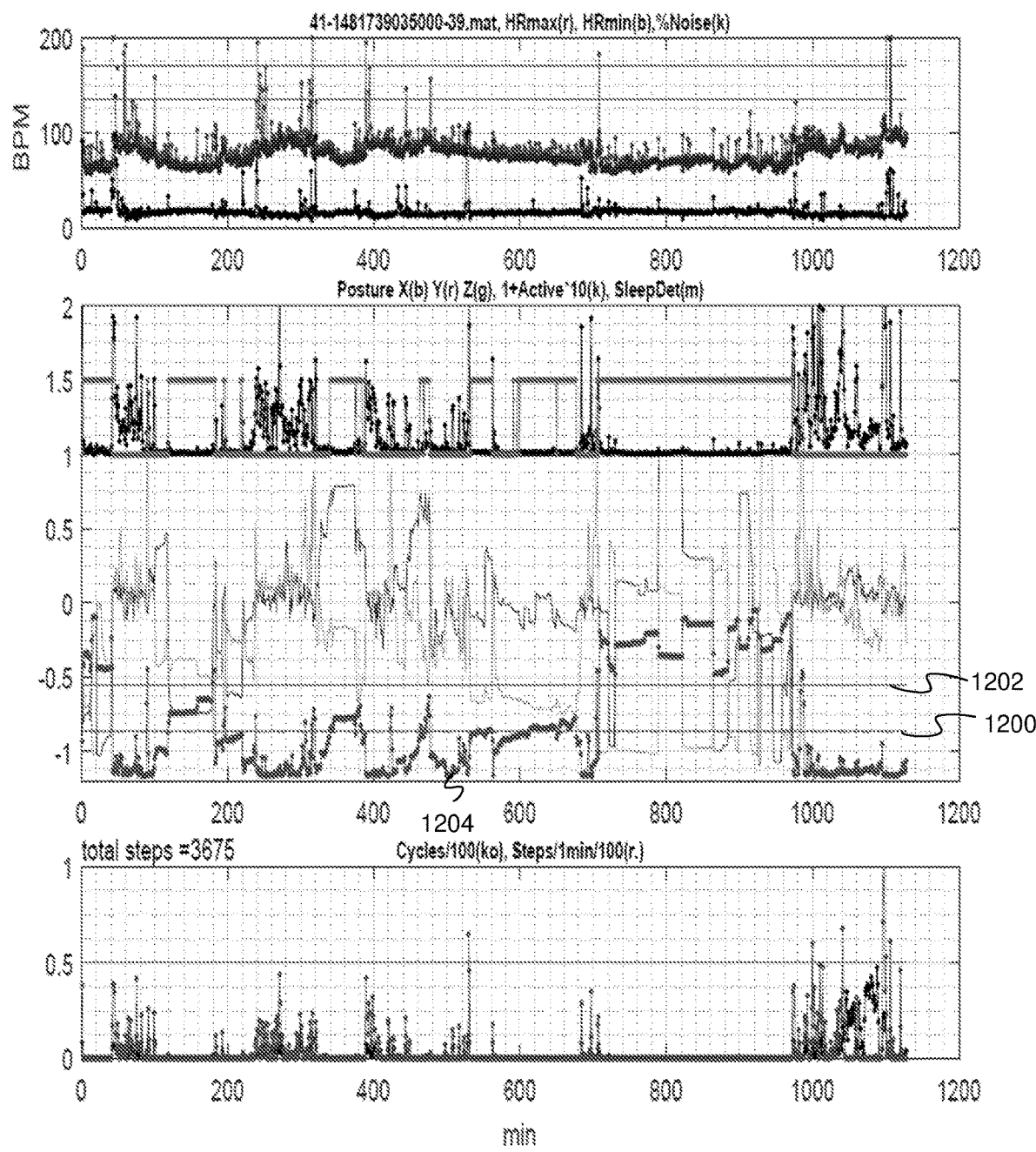
FIG. 12 illustrates another example of measured outputs of a patient to determine the patient is in a sleeping state.

FIG. 12 illustrates another example of sleep detection. Lines 1200 and 1202 represent 60 degrees and 30 degrees, respectively. If the Y value, or output of the accelerometer, line 1204, is between lines 1200 and 1202, then the patient is considered to be in a raised position. The Y value, however, does not allow the processor 230 to differentiate between leaning backwards and leaning forwards. To do such, the Z value of the accelerometer may be used. If the Z value is greater than 0.5 G, then the patient is leaning forward and the processor 230 determines the patient is not asleep.

In some embodiments, as mentioned above, the processor 230 may also use a signal from another sensor to confirm the patient is asleep, such as a light sensor, a clock, a respiration sensor, a sound sensor, etc. If more than one of these sensors are present, the processor 230 may poll each of the sensors for an aggregate score and compare the score to saved score in memory to determine the patient is asleep.

A light sensor, for example, may indicate the ambience of a room since most patients sleep in darker environments. Further, a history of the ambience may be taken to help with the determination of the patient's sleep state. A clock may also indicate the time of day and have an accumulated history indicating what time of day the patient is normally asleep. The respiration rate and pattern may also be used, as well as a sound sensor that can indicate a sleep sound of the patient, such as snoring, for example. Each of these sensors may accumulate a history to help the processor 230 accurately detect that the patient is in a sleeping state.

In some embodiments, after sleep has been detected, the patient may take a short break, such as a bathroom break, without the processor 230 indicating that the patient has woken up. For example, if the processor 230 determines that the patient is asleep, and the patient then gets up for less than 3 minutes, the processor 230 does not disrupt the sleep state, and may extend the response time if a shock is advised.

In embodiments discussed above, when the processor 230 determines the patient is in a lying position, if the signal from the motion sensor indicates that patient has been tossing and turning more than 5 times from the beginning of the lying position, then the sleep state is not detected until the patient has been lying still for a predetermined amount of time, such as 30 minutes.

As would be understood by one skilled in the art, the processor 230 is able to perform the processes discussed above in FIGS. 7 and 9 simultaneously. That is, based on the detected position, movement, or lack thereof by the patient, the processor 230 can determine a state of the patient, such as having fallen or sleeping, and determine either a confirmation time and/or a response time based on the state of the patient.

Aspects and examples of the disclosure may operate on particularly created hardware, firmware, digital signal processors, or on a specially programmed computer including a processor operating according to programmed instructions. The terms controller or processor as used herein are intended to include microprocessors, microcomputers, Application Specific Integrated Circuits (ASICs), and dedicated hardware controllers. One or more aspects of the disclosure may be embodied in computer-usable data and computer-executable instructions, such as in one or more program modules, executed by one or more computers (including monitoring modules), or other devices. Generally, program modules include routines, programs, objects, components, data structures, etc. that perform particular tasks or implement particular abstract data types when executed by a processor in a computer or other device. The computer executable instructions may be stored on a computer readable storage medium such as a hard disk, optical disk, removable storage media, solid state memory, Random Access Memory (RAM), etc. As will be appreciated by one of skill in the art, the functionality of the program modules may be combined or distributed as desired in various aspects. In addition, the functionality may be embodied in whole or in part in firmware or hardware equivalents such as integrated circuits, field programmable gate arrays (FPGA), and the like. Particular data structures may be used to more effectively implement one or more aspects of the disclosure, and such data structures are contemplated within the scope of computer executable instructions and computer-usable data described herein.

The disclosed aspects and examples may be implemented, in some cases, in hardware, firmware, software, or any combination thereof. The disclosed aspects may also be implemented as instructions carried by or stored on one or more computer-readable storage media, which may be read and executed by one or more processors. Such instructions may be referred to as a computer program product. Computer-readable media, as discussed herein, means any media that can be accessed by a computing device. By way of example, and not limitation, computer-readable media may comprise computer storage media and communication media.

Computer storage media means any medium that can be used to store computer-readable information. By way of example, and not limitation, computer storage media may include RAM, ROM, Electrically Erasable Programmable Read-Only Memory (EEPROM), flash memory or other memory technology, Compact Disc Read Only Memory (CD-ROM), Digital Video Disc (DVD), or other optical disk storage, magnetic cassettes, magnetic tape, magnetic disk storage or other magnetic storage devices, and any other volatile or nonvolatile, removable or non-removable media implemented in any technology. Computer storage media excludes signals per se and transitory forms of signal transmission.

Communication media means any media that can be used for the communication of computer-readable information. By way of example, and not limitation, communication media may include coaxial cables, fiber-optic cables, air, or any other media suitable for the communication of electrical, optical, Radio Frequency (RF), infrared, acoustic or other types of signals.

Aspects and examples of the present disclosure operate with various modifications and in alternative forms. Specific aspects have been shown by way of example in the drawings and are described in detail herein below. However, it should be noted that the examples disclosed herein are presented for the purposes of clarity of discussion and are not intended to limit the scope of the general concepts disclosed to the specific examples described herein unless expressly limited. As such, the present disclosure is intended to cover all modifications, equivalents, and alternatives of the described aspects in light of the attached drawings and claims.

References in the specification to embodiment, aspect, example, etc., indicate that the described item may include a particular feature, structure, or characteristic. However, every disclosed aspect may or may not necessarily include that particular feature, structure, or characteristic. Moreover, such phrases are not necessarily referring to the same aspect unless specifically noted. Further, when a particular feature, structure, or characteristic is described regarding a particular aspect, such feature, structure, or characteristic can be employed in connection with another disclosed aspect whether or not such feature is explicitly described in conjunction with such other disclosed aspect.

EXAMPLES

Illustrative examples of the technologies disclosed herein are provided below. An embodiment of the technologies may include any one or more, and any combination of, the examples described below.

Example 1 is a wearable cardioverter defibrillator (WCD), comprising a support structure configured to be worn by an ambulatory patient; an energy storage module configured to store an electrical charge; a discharge circuit coupled to the energy storage module; electrodes configured to render an electrocardiogram (ECG) signal of the patient while the ambulatory patient is wearing the support structure; a user interface configured to output an alarm in response to a shock alert signal; a motion sensor configured to output a signal indicating a position and/or movement of the ambulatory patient while the ambulatory patient is wearing the support structure; and a processor. The processor is configured to receive the signal from the motion sensor, receive the ECG signal, determine from the ECG signal whether a shock criterion is met, determine a confirmation time period based on the position and/or movement of the ambulatory patient, determine from the ECG signal whether the shock criterion is met after the confirmation time period has elapsed, cause the user interface to generate the shock alert signal based on the shock criterion determined after the confirmation time period has elapsed, and control the discharge circuit to discharge the stored electrical charge when a predetermined time period has elapsed after the shock alert signal.

Example 2 is the WCD of example 1, wherein the processor is further configured to:

detect a patient fall in response to the signal from the motion sensor indicating a positional change of the patient from an upright position to a sitting or supine position that violates a positional change threshold, and determine the confirmation time period based on the detected patient fall.

Example 3 is the WCD of example 2, wherein the positional change threshold includes a positional change time period or a positional change force, and the patient fall is detected in response to the positional change being less than the positional change time period or greater than the positional change force.

Example 4 is the WCD of example 2 or 3, wherein the processor is further configured to detect whether a patient remains motionless based on the signal from the motion sensor after the detected patient fall, and determine the confirmation time period based on whether the patient remains motionless.

Example 5 if the WCD of example 4, wherein the confirmation time period is shorter when the patient fall has been detected and the patient has remained motionless after the detected patient fall than when the patient fall has been detected and the patient has not remained motionless after the detected patient fall.

Example 6 is the WCD of any one of examples 1-5, wherein the predetermined time period is a response time period and the processor is further configured to determine the response time period based on the detected fall and an amount of movement of the patient after the detected fall, and control the discharge circuit to discharge the stored electrical charge when the response time period has elapsed after the shock alert signal and a user response has not been received.

Example 7 is the WCD of example 6, wherein the response time period is shorter when no movement is detected based on the signal from the motion sensor after the detected fall and the response time period is longer when movement is detected based on the signal from the motion sensor after the detected fall.

Example 8 is the WCD of any one of examples 1-7, wherein the processor is further configured to detect noise on the ECG signal and determine the confirmation time period based on the detected noise.

Example 9 is the WCD of any one of examples 1-8, further comprising a transmitter configured to output an alert to a remote center when the confirmation time period has elapsed and a user input has not been received at the user interface.

Example 10 is the WCD of any one of examples 1-9, wherein the motion sensor is an accelerometer.

Example 11 is the WCD of any one of examples 1-10, wherein the processor is further configured to determine the confirmation time period by selecting the confirmation time period from a plurality of confirmation time periods based on the position and/or movement of the ambulatory patient Example 12 is a wearable cardioverter defibrillator (WCD), comprising a support structure configured to be worn by an ambulatory patient; an energy storage module configured to store an electrical charge; a discharge circuit coupled to the energy storage module; electrodes configured to render an electrocardiogram (ECG) signal of the patient while the patient is wearing the support structure; a user interface configured to output an alarm in response to a shock alert signal; a motion sensor configured to output a signal indicating a position and/or movement of the ambulatory patient while the patient is wearing the support structure; and a processor. The processor is configured to receive the signal from the motion sensor, receive the ECG signal, determine from the ECG signal whether a shock criterion is met, cause the user interface to generate the shock alert signal based on the shock criterion, determine a response time period based on the position and/or movement of the ambulatory patient, and in a first mode, control the discharge circuit to discharge the stored electrical charge after the response time period has elapsed and a user input has not been received at the user interface, and in a second mode not control the discharge circuit to discharge the stored electrical charge after the user input has been received at the user interface prior to the response time elapsing.

Example 13 is the WCD of example 12, wherein the processor is further configured to detect a sleeping state of the patient based on the signal from the motion sensor indicating the patient is in a lying position for greater than a minimum time period, and determine the response time period based on the sleeping state.

Example 14 is the WCD of example 13, wherein the minimum time period is thirty minutes.

Example 15 is the WCD of example 13 or 14, wherein the sleeping state is maintained when the signal from the motion sensor detects a patient in an upright position for less than three minutes.

Example 16 is the WCD of any one of examples 13-15, wherein the minimum time period does not begin until less than five position changes are detected after detecting the patient is in the lying position.

Example 17 is the WCD of any one of examples 13-16, wherein the response time period is greater when the sleeping state is detected than when the sleeping state is not detected.

Example 18 is the WCD of any one of examples 13-17, wherein the processor is further configured to detect the sleeping state of the patient based on the motion of the patient determined by the signal from the motion sensor.

Example 19 is the WCD of any one of examples 13-18, further comprising a light sensor configured to output a signal indicating an ambience, and wherein the processor is further configured to detect the sleeping state of the patient based on the ambience.

Example 20 is the WCD of any one of examples 13-19, further comprising a clock to indicate a time of day, wherein the processor is further configured to detect the sleeping state of the patient based on the time of day.

Example 21 is the WCD of any one of examples 13-19, further comprising a sound sensor configured to output a signal indicating sleeping sounds of a patient, wherein the processor is further configured to detect the sleeping state of the patient based on the sleeping sounds.

Example 22 is the WCD of any one of examples 13-21, further comprising a respiratory sensor to output a signal indicating a respiration rate; and a memory configured to store the signal indicating the respiration rate for a period of time, wherein the processor is further configured to detect the sleeping state of the patient based on the signal indicating the respiration rate and the stored respiration rate.

Example 23 is the WCD of any one of examples 13-22, wherein the processor is further configured to determine a heart rate of the patient, and detect the sleeping state of the patient based on the heart rate of the patient and the signal from the motion sensor indicating the patient is in the lying position.

Example 24 is the WCD of any one of examples 12-23, wherein the processor is further configured to determine the patient is in a reclined position based on the signal from the motion sensor; determine an amount of time the patient has been in the reclined position without movement based on the signal from the motion sensor; and detect a sleeping state of the patient based on the amount of time the patient has been in the reclined position without movement based on the signal from the motion sensor.

Example 25 is the WCD of example 24, wherein the processor is further configured to detect the sleeping state of the patient based on the movement of the patient determined by the signal from the motion sensor.

Example 26 is the WCD of example 24 or 25, further comprising a light sensor configured to output a signal indicating an ambience, and wherein the processor is further configured to detect the sleeping state of the patient based on the ambience.

Example 27 is the WCD of any one of examples 24-26, further comprising a clock to indicate a time of day, wherein the processor is further configured to detect the sleeping state of the patient based on the time of day.

Example 28 is the WCD of any one of examples 24-27, further comprising a sound sensor configured to output a signal indicating a sleeping sound, wherein the processor is further configured to detect the sleeping state of the patient based on the sleeping sound.

Example 29 is the WCD of any one of examples 24-28, further comprising a respiratory sensor to output a signal indicating a respiration rate; and a memory configured to store the signal indicating the respiration rate for a period of time, wherein the processor is further configured to detect the sleeping state of the patient based on the signal indicating the respiration rate and the stored respiration rate.

Example 30 is the WCD of any one of examples 24-29, wherein the processor is further configured to determine a heart rate of the patient, and detect the sleeping state of the patient based on the heart rate of the patient and the signal from the motion sensor indicating the patient is in the lying position.

Example 31 is the WCD of any one of examples 24-30, wherein the minimum time period is thirty minutes.

Example 32 is the WCD of any one of examples 24-31, wherein the processor is further configured to maintain the sleeping state when the signal from the motion sensor detects a patient in an upright position for less than three minutes.

Example 33 is the WCD of any one of examples 24-33, wherein the minimum time period does not begin until less than five position changes are detected after detecting the patient is in the lying position.

Example 34 is the WCD of any one of examples 24-33, wherein the response time period is extended when the sleeping state is detected.

Example 35 is the WCD of any one of examples 24-34, wherein the motion sensor is an accelerometer.

Example 36 is the WCD of any one of examples 24-35, wherein the processor is further configured to determine the response time period by selecting the response time period from a plurality of response time periods based on the position and/or movement of the ambulatory patient.

Example 37 is a method for determining a confirmation time for a shock advisory of a wearable cardioverter defibrillator (WCD), comprising rendering an electrocardiogram (ECG) signal of the patient while the ambulatory patient is wearing a support structure; outputting a signal indicating a position and/or movement of the ambulatory patient while the ambulatory patient is wearing the support structure; determining from the ECG signal whether a shock criterion is met; determining a confirmation time period based on the position and/or movement of the ambulatory patient; determining from the ECG signal whether the shock criterion is met after the confirmation time period has elapsed; causing the user interface to generate a shock alert alarm based on the shock criterion determined after the confirmation time period has elapsed; and discharging a stored electrical charge when a predetermined time period has elapsed after the shock alert signal.

Example 38 is the method of example 37, further comprising detecting a patient fall in response to the signal from the motion sensor indicating a positional change of the patient from an upright position to a sitting or supine position that violates a positional change threshold, and determining the confirmation time period based on the detected patient fall.

Example 39 is the method of example 38, wherein the positional change threshold includes a positional change time period or a positional change force, and the patient fall is detected in response to the positional change being less than the positional change time period or greater than the positional change force.

Example 40 is the method of example 38 or 39, further comprising detecting whether a patient remains motionless based on the signal from the motion sensor after the detected patient fall, and determining the confirmation time period based on whether the patient remains motionless.

Example 41 is the method of example 40, wherein the confirmation time period is shorter when the patient fall has been detected and the patient has remained motionless after the detected patient fall than when the patient fall has been detected and the patient has not remained motionless after the detected patient fall.

Example 42 is the method of any one of examples 37-41, wherein the predetermined time period is a response time period and the method is further comprising determining the response time period based on the detected fall and an amount of movement of the patient after the detected fall; and controlling the discharge circuit to discharge the stored electrical charge when the response time period has elapsed after the shock alert signal and a user response has not been received.

Example 43 is the method of any one of examples 37-42, wherein the response time period is shorter when no movement is detected based on the signal from the motion sensor after the detected fall and the response time period is longer when movement is detected based on the signal from the motion sensor after the detected fall.

Example 44 is the method of any one of examples 37-43, further comprising detecting noise on the ECG signal and determining the confirmation time period based on the detected noise.

Example 45 is the method of any one of examples 37-44, further comprising outputting an alert to a remote center when the confirmation time period has elapsed and a user input has not been received at the user interface.

Example 46 is the method of any one of examples 37-45, wherein the motion sensor is an accelerometer.

Example 47 is the method of any one of examples 37-46, further comprising determining the confirmation time period by selecting the confirmation time period from a plurality of confirmation time periods based on the position and/or movement of the ambulatory patient Example 48 is a method for determining a response time of a wearable cardioverter defibrillator (WCD), comprising receiving a signal from a motion sensor indicating a position and/or movement of the ambulatory patient while the patient is wearing the support structure; receiving an electrocardiogram (ECG) signal of the patient while the patient is wearing the support structure; determining from the ECG signal whether a shock criterion is met; generating a shock alert signal based on the shock criterion; determining a response time period based on the position and/or movement of the ambulatory patient; and in a first mode, controlling a discharge circuit to discharge a stored electrical charge after the response time period has elapsed and a user input has not been received at a user interface, and in a second mode not controlling the discharge circuit to discharge the stored electrical charge after the user input has been received at the user interface prior to the response time elapsing.

Example 49 is the method of example 48, further comprising detecting a sleeping state of the patient based on the signal from the motion sensor indicating the patient is in a lying position for greater than a minimum time period, and determining the response time period based on the sleeping state.

Example 50 is the method of example 49, wherein the minimum time period is thirty minutes.

Example 51 is the method of example 49 or 50, wherein the sleeping state is maintained when the signal from the motion sensor detects a patient in an upright position for less than three minutes.

Example 52 is the method of any one of examples 49-51, wherein the minimum time period does not begin until less than five position changes are detected after detecting the patient is in the lying position.

Example 53 is the method of any one of examples 49-52, wherein the response time period is greater when the sleeping state is detected than when a sleeping state is not detected.

Example 54 is the method of any one of examples 49-53, further comprising detecting the sleeping state of the patient based on the motion of the patient determined by the signal from the motion sensor.

Example 55 is the method of any one of examples 49-54, further comprising detecting the sleeping state of the patient based on a signal from a light sensor.

Example 56 is the method of any one of examples 49-55, further comprising detecting the sleeping state of the patient based on a time of day.

Example 57 is the method of any one of examples 49-56, further comprising detecting the sleeping state of the patient based on a signal from a sound sensor.

Example 58 is the method of any one of examples 49-57, further comprising detecting the sleeping state of the patient based on a signal indicating the respiration rate and a stored respiration rate.

Example 59 is the method of any one of examples 49-58, further comprising determining a heart rate of the patient, and detecting the sleeping state of the patient based on the heart rate of the patient and the signal from the motion sensor indicating the patient is in the lying position.

Example 60 is the method of any one of examples 48-59, further comprising determining the patient is in a reclined position based on the signal from the motion sensor; determining an amount of time the patient has been in the reclined position without movement based on the signal from the motion sensor; and detecting a sleeping state of the patient when the amount of time the patient has been in the reclined position without movement is greater than a minimum time period.

Example 61 is the method of example 60, further comprising detecting the sleeping state of the patient based on the movement of the patient determined by the signal from the motion sensor.

Example 62 is the method of example 60 or 61, further comprising detecting the sleeping state of the patient based on a signal from a light sensor.

Example 63 is the method of any one of examples 60-62, further comprising detecting the sleeping state of the patient based on a time of day.

Example 64 is the method of any one of examples 60-63, further comprising detecting the sleeping state of the patient based on a signal from a sound sensor.

Example 65 is the method of any one of examples 60-64, further comprising detecting the sleeping state of the patient based on a signal indicating the respiration rate and a stored respiration rate.

Example 66 is the method of any one of examples 60-65, further comprising determining a heart rate of the patient, and detecting the sleeping state of the patient based on the heart rate of the patient and the signal from the motion sensor indicating the patient is in the lying position.

Example 67 is the method of any one of examples 60-66, wherein the minimum time period is thirty minutes.

Example 68 is the method of any one of examples 60-67, further comprising maintaining the sleeping state when the signal from the motion sensor detects a patient in an upright position for less than three minutes.

Example 69 is the method of any one of examples 60-68, wherein the minimum time period does not begin until less than five position changes are detected after detecting the patient is in the lying position.

Example 70 is the method of any one of examples 60-69, wherein the response time period is extended when the sleeping state is detected.

Example 71 is the method of any one of examples 60-70, wherein the motion sensor is an accelerometer.

Example 72 is the method of any one of examples 60-70, further comprising determining the response time period by selecting the response time period from a plurality of response time periods based on the position and/or movement of the ambulatory patient The previously described versions of the disclosed subject matter have many advantages that were either described or would be apparent to a person of ordinary skill. Even so, these advantages or features are not required in all versions of the disclosed apparatus, systems, or methods.

Additionally, this written description makes reference to particular features. It is to be understood that the disclosure in this specification includes all possible combinations of those particular features. Where a particular feature is disclosed in the context of a particular aspect or example, that feature can also be used, to the extent possible, in the context of other aspects and examples.

Also, when reference is made in this application to a method having two or more defined steps or operations, the defined steps or operations can be carried out in any order or simultaneously, unless the context excludes those possibilities.

Although specific examples of the disclosure have been illustrated and described for purposes of illustration, it will be understood that various modifications may be made without departing from the spirit and scope of the disclosure. Accordingly, the disclosure should not be limited except as by the appended claims.

The embodiments of the invention in which an exclusive property or privilege is claimed are defined as follows:

1. A wearable cardioverter defibrillator (WCD), comprising:
   a support structure configured to be worn by an ambulatory patient;
   an energy storage module configured to store an electrical charge;
   a discharge circuit coupled to the energy storage module;
   electrodes configured to render an electrocardiogram (ECG) signal of the patient while the ambulatory patient is wearing the support structure;
   a user interface configured to output an alarm in response to a shock alert signal;
   a motion sensor configured to output a signal indicating a position and/or movement of the ambulatory patient while the ambulatory patient is wearing the support structure; and
   a processor configured to:
      receive the signal from the motion sensor,
      receive the ECG signal,
      determine from the ECG signal whether a shock criterion is met;
      determine a confirmation time period based on the position and/or movement of the ambulatory patient,
      determine from the ECG signal whether the shock criterion is met after the confirmation time period has elapsed,
      cause the user interface to generate the shock alert signal based on the shock criterion determined after the confirmation time period has elapsed, and
      control the discharge circuit to discharge the stored electrical charge when a predetermined time period has elapsed after the shock alert signal.

2. The WCD of claim 1, wherein the processor is further configured to:
   detect a patient fall in response to the signal from the motion sensor indicating a positional change of the patient from an upright position to a sitting or supine position that violates a positional change threshold, and
   determine the confirmation time period based on the detected patient fall.

3. The WCD of claim 2, wherein the positional change threshold includes a positional change time period or a positional change force, and the patient fall is detected in response to the positional change being less than the positional change time period or greater than the positional change force.

4. The WCD of claim 2, wherein the processor is further configured to:
   detect whether a patient remains motionless based on the signal from the motion sensor after the detected patient fall, and
   determine the confirmation time period based on whether the patient remains motionless.

5. The WCD of claim 4, wherein the confirmation time period is shorter when the patient fall has been detected and the patient has remained motionless after the detected patient fall than when the patient fall has been detected and the patient has not remained motionless after the detected patient fall.

6. The WCD of claim 1, wherein the predetermined time period is a response time period and the processor is further configured to determine the response time period based on the detected fall and an amount of movement of the patient after the detected fall, and control the discharge circuit to discharge the stored electrical charge when the response time period has elapsed after the shock alert signal and a user response has not been received.

7. The WCD of claim 6, wherein the response time period is shorter when no movement is detected based on the signal from the motion sensor after the detected fall and the response time period is longer when movement is detected based on the signal from the motion sensor after the detected fall.

8. The WCD of claim 1, wherein the processor is further configured to detect noise on the ECG signal and determine the confirmation time period based on the detected noise.

9. The WCD of claim 1, further comprising a transmitter configured to output an alert to a remote center when the confirmation time period has elapsed and a user input has not been received at the user interface.

10. The WCD of claim 1, wherein the motion sensor is an accelerometer.

11. The WCD of claim 1, wherein the processor is further configured to determine the confirmation time period by selecting the confirmation time period from a plurality of confirmation time periods based on the position and/or movement of the ambulatory patient.

* * * * *